United States Patent [19]

Hove

[11] Patent Number: 5,388,141
[45] Date of Patent: Feb. 7, 1995

[54] X-RAY APPARATUS COMPRISING AN APPARATUS SECTION WHICH IS PIVOTABLE ABOUT A HORIZONTAL PIVOTAL AXIS

[75] Inventor: Ulrich Hove, Norderstedt, Germany

[73] Assignee: U.S. Philips Corporation, New York, N.Y.

[21] Appl. No.: 182,257

[22] Filed: Jan. 14, 1994

[30] Foreign Application Priority Data

Jan. 14, 1993 [DE] Germany .................... 4300796

[51] Int. Cl.⁶ .............................................. A61B 6/04
[52] U.S. Cl. ...................................... 378/197; 378/37; 378/196
[58] Field of Search .............. 378/37, 195, 196, 197, 378/193, 198, 167, 177, 179

[56] References Cited

U.S. PATENT DOCUMENTS

| 3,770,955 | 11/1973 | Tomita et al. | 378/197 X |
| 4,813,064 | 3/1989 | Jackson, III et al. | 378/197 |
| 4,989,228 | 1/1991 | Louiday | 378/196 |
| 5,170,420 | 12/1992 | Warden | 378/197 X |

FOREIGN PATENT DOCUMENTS 0498255 8/1992 European Pat. Off. .

Primary Examiner—David P. Porta
Attorney, Agent, or Firm—Jack D. Slobod

[57] ABSTRACT

The invention relates to an X-ray apparatus, including an apparatus section which is pivotable about a horizontal pivotal axis that does not extend through its center of gravity, and a spring assembly for compensation of the torque which is exerted by the weight of the apparatus section on a coupling member which moves in an orbit about the pivotal axis during pivoting of the apparatus section. Suitable counterbalancing is readily achieved in that the center of the orbit is situated outside the pivotal axis in a vertical plane containing the pivotal axis and that the coupling member is guided in a guide device which is connected to the apparatus section and which extends towards the pivotal axis.

8 Claims, 1 Drawing Sheet

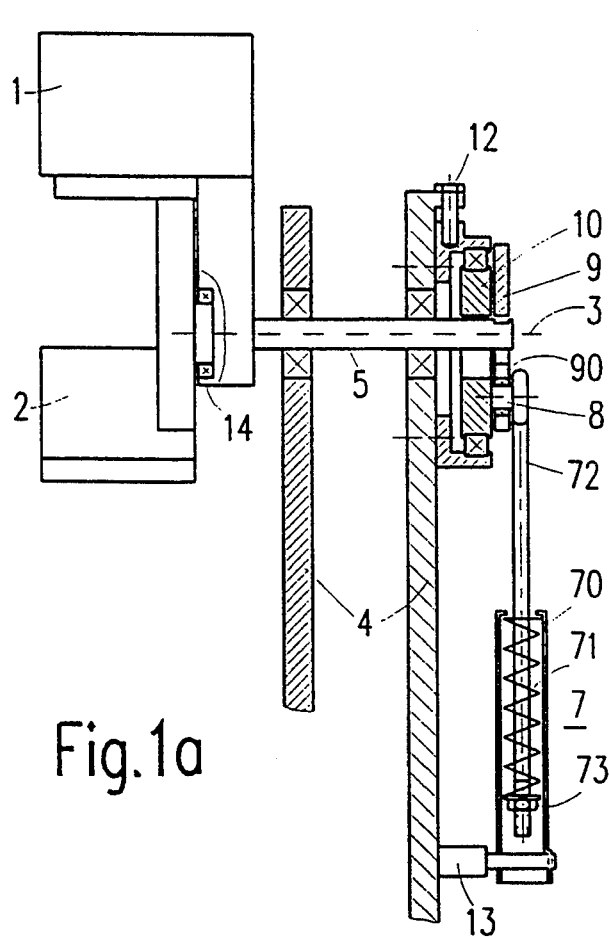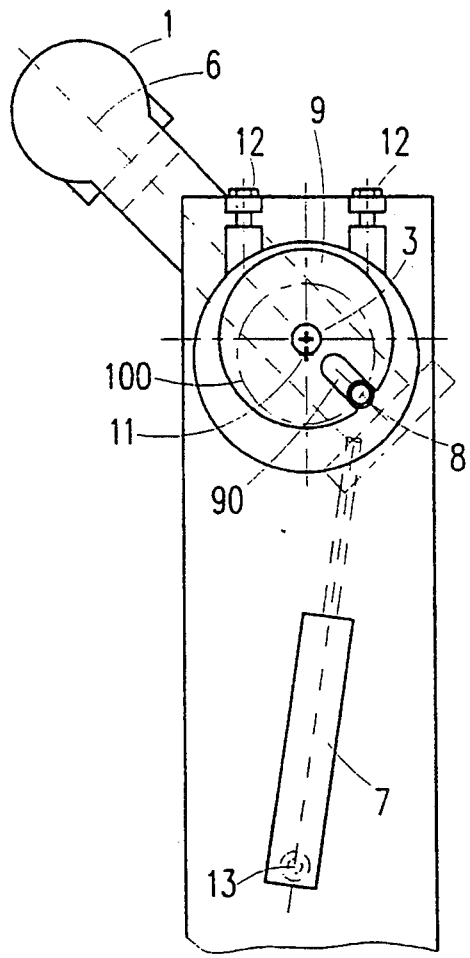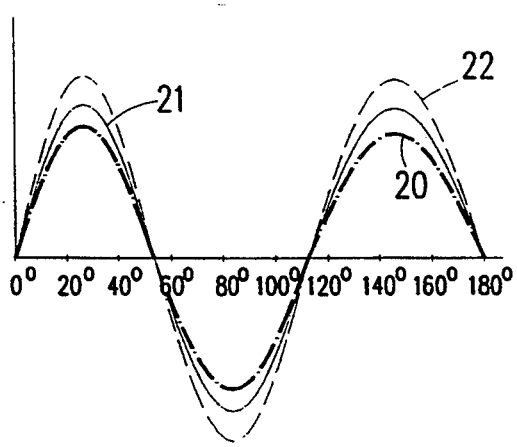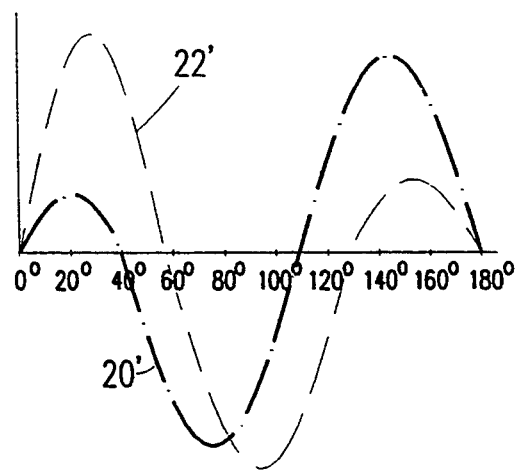

X-RAY APPARATUS COMPRISING AN APPARATUS SECTION WHICH IS PIVOTABLE ABOUT A HORIZONTAL PIVOTAL AXIS

BACKGROUND OF THE INVENTION

1. Field of the Invention

The invention relates to an X-ray apparatus, including an apparatus section which is pivotable about a horizontal pivotal axis that does not extend through its centre of gravity, and a counterbalance spring assembly for compensation of the torque which is exerted by the weight of the apparatus section on a coupling member which moves in an orbit about the pivotal axis during pivoting of the apparatus section. Compensated for so that counterbalancing has been achieved, an operator can also pivot a heavy apparatus section with little effort.

2. Description of the Related Art

An X-ray apparatus of this kind is known from EP-A1-0 498 255. In the known X-ray apparatus, the apparatus section, being an X-ray unit of a mammography apparatus, is rigidly connected to a crank-like coupling member which moves in an orbit about the pivotal axis during pivoting of the apparatus section. The coupling member acts, via a roller, on a member which comprises a horizontal running surface for the roller and which can be displaced in the vertical direction. A counterbalancing system acts on this member. When the balancing force delivered by this system is constant, the torque exerted by the apparatus section relative to the pivotal axis can be compensated for, provided that a suitable design has been chosen. A constant balancing force could be delivered by a counterbalancing weight.

However, when the counterbalancing system utilizes a spring assembly, the latter changes its length during pivoting of the apparatus section, and hence the force produced by the counterbalancing system also changes. The torque, however, can then still be fully compensated for in one or two pivotal positions. Moreover, in the known X-ray apparatus the counterbalancing system serves not only to compensate for the torque exerted during pivoting of the apparatus section, but also for the weight of the apparatus section. The force delivered by the counterbalancing system, therefore, should correspond to the weight of the apparatus section or, when the system is connected to the section via a system of pulleys, it should relate to the force according to an integer ratio. In each case the variation of the length of the spring assembly corresponds to the displacement of the apparatus section in the vertical direction. Therefore, it can be comparatively large and cause correspondingly large variations of the spring force produced by the counterbalancing system, so that the torque produced for compensation may deviate substantially from the moment exerted by the apparatus section.

SUMMARY OF THE INVENTION

It is an object of the present invention to construct an X-ray apparatus of the kind set forth so that the torque produced during the pivoting of the apparatus section can be compensated for in a simple and comparatively accurate manner.

This object is achieved in that the centre of the orbit is situated outside the pivotal axis in a vertical plane containing the pivotal axis, the coupling member being guided in a guide device which is connected to the apparatus section and which extends towards the pivotal axis. Thus, in accordance with the invention the centre of the orbit does not coincide with the pivotal axis but is situated in a vertical plane containing the pivotal axis. As a result, suitable counterbalancing is achieved also for a comparatively wide range of pivotal angles. Because the coupling member moves along a path which is eccentric relative to the pivotal axis, the guide device ensures that the coupling member is always situated on the line connecting the centre of gravity of the apparatus section to the pivotal axis.

For displacement of the coupling member along an orbit which is eccentric relative to the pivotal axis, there could be provided a crank arm which is connected to the coupling member and which is pivotable about a second axis extending parallel to the pivotal axis. In that case, however, the pivotal range for the apparatus section would be limited. In an embodiment of the invention such limitations are avoided in that the coupling member is connected to a carrier which is journalled in a bearing ring whose central axis does not coincide with the pivotal axis.

In another embodiment of the invention, the coupling member and the centre of gravity of the apparatus section are situated at different sides of the pivotal axis, the centre of the orbit being situated below the pivotal axis. If the coupling member and the apparatus section were situated at the same side of the pivotal axis, the centre of the orbit should be situated above the pivotal axis.

In an embodiment of the invention there are provided adjusting means for adjusting the distance between the centre of the orbit and the pivotal axis, which adjusting means are constructed so that they define a vertical plane also when the centre and the pivotal axis are readjusted. The difference between the torque produced by the apparatus section relative to the pivotal axis and the torque produced for compensation by the spring assembly depends not only on the pivotal position but also on the spring characteristic, notably on the spring constant. When coil springs are used, however, manufacturing tolerances of the order of 15% may occur in respect of the spring constant. Counterbalancing can be adapted to different spring constants by adjustment of the distance between the centre of the orbit and the pivotal axis.

In a preferred embodiment of the invention the apparatus section constitutes the X-ray unit of a mammography apparatus comprising an X-ray source and an object positioning unit, the X-ray source being pivotable about the pivotal axis, as desired, either together with the object positioning unit or independently therefrom, the pivotal axis extending through the centre of gravity of the object positioning unit. Counterbalancing is then independent of whether the X-ray apparatus is pivoted together with the object positioning unit or independently therefrom (the latter is important for biopsies).

BRIEF DESCRIPTION OF THE DRAWING

The invention will be described in detail hereinafter with reference to the drawings. Therein:

FIG. 1a is a diagrammatic side elevation of an X-ray examination apparatus in accordance with the invention.

FIG. 1b is a rear view of the same apparatus.

FIG. 2a shows the difference between the torque of the apparatus section and the compensating torque as a function of the angular position in the case of optimum adjustment.

FIG. 2b shows the difference as a function of the pivotal angle for different spring constants in the case of non-optimum adjustment.

DETAILED DESCRIPTION OF THE PREFERRED EMBODIMENTS

FIGS. 1a and 1b show a section of an X-ray examination apparatus for mammography in a side elevation and a rear view, respectively. The apparatus section, to be pivoted about a horizontal axis, is in this case formed by an X-ray unit which comprises an X-ray source 1 and an object positioning unit 2. This unit is journalled in a stand 4 so as to be pivotable about a horizontal axis 3, only part of the supporting walls of said stand being shown. The X-ray unit 1, 2 is connected to a shaft 5 whose central axis constitutes the pivotal axis 3 and which is journalled in the stand.

As in the apparatus according to EP-A1-498 255, the pivotal axis is situated approximately at the centre of an object to be examined. Because the X-ray source 1, however, is substantially heavier than the object positioning unit 2, the pivotal axis 3 does not extend through the centre of gravity; this centre is situated nearer to the X-ray source 1. As soon as the plane which connects the pivotal axis 3 to the centre of gravity and which is denoted by the reference 6 in FIG. 1b does not extend vertically, the X-ray unit 1, 2 will exert a torque relative to the axis 3.

For counterbalancing, i.e. for compensation of this torque, there is provided a spring assembly 7 which is pivotable about a trunnion 13 which extends parallel to the shaft 5, is situated below the shaft 5, and defines a vertical plane in conjunction therewith; consequently, the counterbalancing properties are independent of whether the unit 1, 2 is pivoted to the left or to the right. The spring assembly 7 comprises a spring housing 70 accommodating a coil spring 71; the spring force of a coil spring is substantially linearly dependent on the spring excursion. The coil spring 71 encloses a rod 72 which passes through an opening in the upper end face of the housing 70, its lower end being provided with a screw thread. The upper end of the coil spring 71 is pressed against the end face, the bias of this coil spring 71 being adjustable by means of a nut 73. Even though the coil spring is thus compressed, a pulling force is thus exerted on the rod 72.

This pulling force is transferred from the rod 72 to a coupling member 8 in the form of a trunnion which is situated in the plane 6. The coupling member 8 is guided in a slot 90 which extends perpendicularly to the pivotal axis in a flange 9 connected to the shaft 5, so that it can move to and fro the pivotal axis 3 in the plane 6. The trunnion 8 is connected to a ring 10 which encloses the shaft 5 and whose central axis extends parallel to the pivotal axis 3. When the source 1 is pivoted, therefore, the trunnion 8 is displaced within the slot 90 and at the same time it moves along an orbit 100 which is perpendicular to the pivotal axis 3. The centre 11 of this orbit and the pivotal axis 3 are situated in a vertical plane, the centre being situated below the pivotal axis 3 in the present embodiment.

The bearing supporting the ring 10 with the trunnion 8 can be adjusted in the vertical direction by means of the adjusting screws 12, so that the position of the orbit 100 or its centre 11 can be adjusted in a vertical plane relative to the pivotal axis 3.

The pulling force exerted on the trunnion 8 by the spring assembly 7 produces a torque about the pivotal axis 3 which opposes the torque exerted by the X-ray unit 1, 2. Therefore, exact compensation of the torques or counterbalancing by suitable proportioning of the spring force, be it not for arbitrary inclinations of the X-ray unit 1, 2.

The torque produced by the X-ray unit 1, 2 is zero for the pivotal angles 0° and 180° (the pivotal angle is the angle between the perpendicular and the plane 6). The same holds for the torque exerted by the spring assembly in these positions. Between 0° and 180° the torque exerted by the unit 1, 2 changes in proportion to the sine of the pivotal angle. The variation of the torque exerted by the spring assembly only approximates such a sinusoidal function, so that exact compensation is not possible for all pivotal angles.

If the centre 11 of the orbit 100 along which the trunnion is movable were to coincide with the pivotal axis, as in the apparatus disclosed in EP-A1-498 255, the spring assembly could be adjusted so that exact compensation of the torques would be achieved also for a further pivotal angle, for example of 90°. For smaller pivotal angles the torque of the unit 1, 2 dominates because the spring 71 is then compressed less so that it produces a smaller pulling force. For larger pivotal angles, however, the torque produced by the spring dominates, because the spring 71 is compressed more and hence exerts a greater pulling force on the trunnion 8. The deviations between the torques may be comparatively large, so that a user can move the unit 1, 2 to a desired position only with some effort.

However, when instead the centre 11 is situated below the pivotal axis 3 as shown in FIG. 1, the distance between the trunnion 8 and the pivotal axis 3 decreases as the pivotal angle increases (as the spring force increases). This enables the counterbalancing to be proportioned so that exact compensation is obtained not only at 0° and 180°, but also for a first and a second pivotal angle (because of the symmetry of the device, the same holds also for the pivoting of the unit 1 from the vertical initial position in the opposite direction). For small pivotal angles the torque of the unit 1, 2 then dominates. In a central range of pivotal angles the torque of the spring assembly dominates; for pivotal angles beyond that, up to 180°, the torque of the unit 1, 2 dominates again. The deviations from the exact compensation of the torques can then be several times smaller than in a device in which the centre 11 and the pivotal axis 3 coincide. Optimum proportioning is obtained when the maximum deviations of the torques from one another are equal in an absolute sense in all three pivotal angle ranges.

This is shown in FIG. 2a which qualitatively shows the variation of the difference between the torques of the X-ray exposure unit 1, 2 and the spring assembly as a function of the pivotal angle (between 0° and 180°). The solid curve 21 has been obtained for a given spring constant after optimization of the distance between the centre 11 and the pivotal axis 3 by means of the adjusting screw 12 and of the spring bias by means of the adjusting screw 73.

Such optimization and its effects will be illustrated on the basis of the following numerical example. For a distance of 500 mm between the centre of gravity of the unit 1, 2 and the pivotal axis 3, its overall mass amounted to 40 kg. The distance between the trunnion 13 and the pivotal axis 3 amounted to 600 mm and the radius of the orbit was 60 mm. For a spring constant of 14N/mm for the pivotal angle range of from 0° to 180° an optimum was obtained for a spring bias (being the minimum spring force occurring when the trunnion is at the lowest point of the orbit) of 2362N and a distance of 9.5 mm between the pivotal axis 3 and the centre 11. The maximum deviation between the torques in that case amounted to approximately 3000N/mm. For the distance given for the centre of gravity, this means that the unit 1, 2 with a weight of 40 kg can be pivoted with a maximum force of 6N. This is acceptible in clinical practice.

FIG. 2a also shows a dashed curve 22 and a dash-dot curve 20. These curves represent the optimum when a spring having a spring constant which is approximately 6.5% larger (curve 22) or smaller (curve 20) is used. This deviation of the spring constant is within the spread in tolerances of commercially available springs. In order to achieve the optimum, the spring bias and the distance between pivotal axis and centre should be adapted to the changed spring constant. In the case of a larger spring constant (curve 22), a lower spring bias is required, but a larger distance between pivotal axis and centre; the reverse situation occurs in the case of a smaller spring constant (curve 20).

However, if only the spring bias were changed in the event of a changed spring constant and the distance between the pivotal axis 3 and the centre 11 were left the same (9.5 mm), in the best case the curves 20' and 22' shown in FIG. 2b would be obtained; these curves are based on the same spring constant as the curves 20 and 22 in FIG. 2a.

It will be evident that for an optimum always the spring constant, the spring bias and said distance must be matched. When one of these three optimization parameters is changed, the deviations increase.

For example, when the distance between the pivotal axis and the centre is chosen to be smaller than the value required for the optimum, the deviations of the torques will become larger for small pivotal angles and smaller for large pivotal angles. This is because, in comparison with the optimized case, the distance between the trunnion 8 and the pivotal axis 3 deceases for small pivotal angles and increases for large pivotal angles, so that the torque produced by the spring assembly is also smaller and larger, respectively. However, if the distance between the centre 11 and the pivotal axis 3 is larger than required for the optimum, the deviations for small pivotal angles become smaller whereas they become larger for large pivotal angles when the other parameters remain the same. When, moreover, the spring bias is slightly increased in the latter case, it is achieved that the deviations increase for small and for large pivotal angles and that they become smaller for the central range of pivotal angles. Consequently, up to the central range of pivotal angles of, for example 110°, deviations occur which are smaller than those that can be obtained with the curves optimized for the entire pivotal angle range from 0° to 180°. This is advantageous when the X-ray unit is not to be pivoted through 180° but, for example only through 90° about the vertical.

The changing of the spring bias while keeping the other optimization parameters unchanged also influences the deviations between the torques. When the spring bias is increased, the spring force increases, the other parameters remaining the same, and hence the torque produced by the spring also increases so that the curves 20 to 22 of FIG. 2a are shifted downwards, i.e. the positive deviations between the torques become smaller and the negative deviations become larger in an absolute sense. However, in response to a reduction of the spring force the curves of FIG. 2a are shifted upwards.

In the system shown in FIG. 1 the pivotal axis is situated between the centre of gravity of the unit 1, 2 and the trunnion 8. Counterbalancing is achieved by exerting a pulling force on the trunnion 8. However, it would also be possible to achieve counterbalancing by exerting a pressure at the area between the pivotal axis 3 and the centre of gravity of the unit 1, 2. To this end, the bearing ring should be rotated through 180° relative to the position shown in FIG. 1b and the spring assembly 7 should act as a pressure spring. However, an optimum corresponding to FIG. 2 could then be achieved only if the centre 11 were situated above the pivotal axis 3.

In the embodiment shown in FIG. 1, for reasons of symmetry the bearing trunnion is situated in a vertical plane containing the pivotal axis 3, that is to say below the pivotal axis. Counterbalancing, however, would also be possible by means of a bearing trunnion 13 journalled above the pivotal axis 3 in said plane; however, the spring assembly 7 should then exert a pressure on the trunnion. The centre 11 should then again be situated below the pivotal axis 3.

For customary X-ray mammography the X-ray source 1 as well as the object positioning unit 2 must be pivoted about the pivotal axis 3. However, for biopsies, where the position of a biopsy needle is recorded from two different perspectives under X-ray control, only the X-ray source 1 need be moved, and the object positioning unit 2 should remain in a defined position, for example below the pivotal axis 3. Therefore, the object positioning unit 2 is rotatably journalled on the shaft 5 by means of a beating 14, whereas the X-ray source 1 is rigidly connected to the shaft 5. The object positioning unit 2 can be rigidly connected to the X-ray source by means of coupling devices (not shown) so that it can be rotated about the pivotal axis 3 together with the X-ray source. In order to enable counterbalancing by means of a single spring assembly in both cases, the object positioning unit 2 must then be journalled at its centre of gravity.

The orbit described by the trunnion 8 in the device described above is situated in a plane extending perpendicularly to the pivotal axis 3. However, it is in principle also possible for the plane containing the orbit to intersect the pivotal axis at an angle other than 90° when the normal to the plane extends horizontally. This is because the distance between the trunnion and the pivotal axis is then reduced for an pivotal angle in the range around 90°, so that the torque produced by the spring decreases in this angular range; consequently, the negative deviations become smaller in this angular range. This could lead to improved counterbalancing; however, the guiding of the trunnion and its connection to the spring would then be substantially more difficult.

I claim:

1. An X-ray apparatus, comprising an apparatus section (1, 2) which is pivotable about a horizontal pivotal axis (3) that does not extend through the centre of gravity of said apparatus section, and also comprising a spring assembly (7) for compensation of the torque which is exerted by the weight of the apparatus section on a coupling member (8) which moves in an orbit (100) about the pivotal axis (3) during pivoting of the apparatus section, characterized in that the centre (11) of the orbit (100) is situated outside the pivotal axis (3) in a vertical plane containing the pivotal axis (3), the coupling member (8) being guided in a guide device (9, 90) which is connected to the apparatus section and which extends towards the pivotal axis.

2. An X-ray apparatus as claimed in claim 1, characterized in that the coupling member (8) is connected to a carrier (10) which is rotatably journalled in a bearing ring whose central axis (11) does not coincide with the pivotal axis (3).

3. An X-ray apparatus as claimed in claim 1, characterized in that the coupling member (8) and the centre of gravity of the apparatus section (1, 2) are situated at different sides of the pivotal axis (3), the centre (11) of the orbit (100) being situated below the pivotal axis (3).

4. An X-ray apparatus as claimed in claim 1, characterized in that there are provided adjusting means (12) for adjusting the distance between the centre (11) of the orbit (100) and the pivotal axis (3), which adjusting means are constructed so that they define a vertical plane also when the centre (11) and the pivotal axis (3) are readjusted.

5. An X-ray apparatus as claimed in claim 1, characterized in that the spring assembly (7) comprises a coil spring (71).

6. An X-ray apparatus as claimed in claim 1, characterized in that there are provided adjusting means (73) for adjusting the bias of the spring assembly (7).

7. An X-ray apparatus as claimed in claim 1, characterized in that the apparatus section is formed by the X-ray unit (1, 2) of a mammography apparatus, comprising an X-ray source (1) and an object positioning unit (2), the X-ray source (1) being pivotable about the pivotal axis (3), as desired, either together with the object positioning unit (2) or independently therefrom, the pivotal axis extending through the centre of gravity of the object positioning unit.

8. An X-ray apparatus as claimed in claim 2, characterized in that the coupling member (8) and the centre of gravity of the apparatus section (1, 2) are situated at different sides of the pivotal axis (3), the centre (11) of the orbit (100) being situated below the pivotal axis (3).

* * * * *